United States Patent [19]

Mousa

[11] Patent Number: 5,980,875
[45] Date of Patent: Nov. 9, 1999

[54] HONEY PREPARATIONS

[76] Inventor: Mahmoud A. Mousa, 1630 Wintercrest, East Lansing, Mich. 48823

[21] Appl. No.: 08/835,417

[22] Filed: Apr. 9, 1997

Related U.S. Application Data

[60] Provisional application No. 60/015,348, Apr. 12, 1996.

[51] Int. Cl.$^6$ ........................................................ A61K 7/06
[52] U.S. Cl. ............................................ 424/70.11; 127/29
[58] Field of Search .......................... 424/70, 11; 127/29

[56] References Cited

U.S. PATENT DOCUMENTS

| | | |
|---|---|---|
| 2,871,129 | 1/1959 | Gollinelli . |
| 4,235,889 | 11/1980 | Evers . |
| 4,670,471 | 6/1987 | Clark ........................................ 514/724 |
| 4,950,475 | 8/1990 | Vishnupad et al. ........................ 424/83 |
| 5,129,877 | 7/1992 | Gallo et al. . |
| 5,407,675 | 4/1995 | Etemad-Moghadam ................ 424/401 |
| 5,422,100 | 6/1995 | Eliaz et al. . |

OTHER PUBLICATIONS

The Sugars of Honey, L.W. Doner, J.Sci. Fd. Agric. 1977.

Bergman et al., "Acceleration of Wound Healing . . . ", American Journal of Surgery, pp. 374–376, vol. 145 (Mar. 1983).

*Primary Examiner*—Nathan M. Nutter
*Attorney, Agent, or Firm*—James Creighton Wray; Meera P. Narasimhan

[57] ABSTRACT

Methods and preparations for overcoming problems associated with the local application of honey are disclosed. The preparations include active ingredients of honey and a base including components selected from the group consisting of oils, gelling agents, emulsifiers and combinations thereof. Although honey is preferably used as is, the active ingredients of honey, including vitamins, sugars, enzymes, hormones, amino acids and minerals, may be extracted from honey or other natural products or synthesized. Potential applications for the present invention include topical treatments for therapeutic, cosmetic and nutritional purposes, including hair growth, hair loss prevention and wound healing.

5 Claims, No Drawings

HONEY PREPARATIONS

This application claims the benefit of U.S. Provisional Application No. 60/015,348, filed Apr. 12, 1996.

BACKGROUND OF THE INVENTION

The present invention relates to methods and products for treating wounds and skin conditions and for stimulating hair growth.

Honey has been shown to have considerable wound and ulcer healing capacity and strong antimicrobial activity. Recognizing those utilities, members of the medical profession have engaged in treatment protocols involving the local application of honey. Wounds and ulcers which were unresponsive to conventional treatments have, when treated with honey, become sterile within one week. In 1980 it was reported that necrotic malignant breast ulcers were effectively treated with honey. Wounds disrupted after Caesarean sections have been shown to heal after application of a thin layer of honey without the need for resuturing. Open wounds, infected wounds, e.g., vulvectomy, infected perineum and infected abdominal wall wounds healed faster when treated with honey than when treated conventionally. Healing processes are generally not hindered by the presence of microorganisms in the honey or in the infected wounds or ulcers. Even when wounds are challenged with high inocula of infectious bacteria, honey remains superior to conventional wound healing medications, with the honey-treated wounds exhibiting less neutrophil infiltration and marked proliferation of angioblasts and fibroblasts. Honey dressings have also proven superior in the treatment of superficial wounds and burns, with patients experiencing increased wound sterilization, earlier healing, more pain relief and less irritation without allergies and other side effects often experienced during conventional healing processes. Honey also appears to promote rapid wound debridement, replacement of sloughs with granulation tissue and rapid epithelialization and absorption of oedema from around the margins.

Honey has great potential for use as a medicinal antimicrobial. That potential has been demonstrated by the tremendous amount of research in that area. Honey exhibits pronounced antimicrobial activity against most pathogenic bacteria and fungi regardless of their susceptibility or resistance to different antibiotics. The antimicrobial activity of honey was attributed to its high sugar osmolarity and low acidity, but honey has been shown to have stronger antimicrobial activity than corresponding sugar concentrations with similar pHs. The antimicrobial activity has also been attributed to the enzymatically liberated hydrogen peroxide activity known as inhibine. It should be noted, however, that some types of honey, such as manuka honey, exhibit marked antibacterial activity in the absence of peroxide activity. Manuka honey is currently being marketed in New Zealand as an antibacterial product.

Honey has revealed moderate antitumor and pronounced metastatic effects when tested in rats; the antitumor activity of 5-fluorouracil and cyclophosphamide is potentiated by honey. Scientific literature has also suggested honey applications for treating cardiovascular diseases, cataracts and bronchial asthma and for preserving graft tissues. Further, honey has proven effective in treating cold sores and herpes simplex on the lips, skin allergies and insect bites.

While honey has proven effective as a treatment, topical application of honey is inconvenient. The stickiness, thinning and liquefaction accompanying existing honey applications are major restrictions to their topical application. Thinning and liquefaction of existing preparations increases honey mobility, resulting in poor dosing. That mobility exacerbates the stickiness problem, as the treatment inevitably drips and spreads to other areas, including clothes. When existing honey applications are applied to exposed tissues such as open wounds or eyes, intense irritation results from the high osmolarity of honey. Needs exist for honey-based treatments having physical characteristics conducive to topical application.

SUMMARY OF THE INVENTION

The present invention includes a honey formulation for topical application. The formulation includes the active ingredients of honey and related products and may take the form of a cream, gel, ointment, paste, lotion or the like. Unlike existing preparations, the present formulation has reduced stickiness and irritability and a controlled consistency. Those characteristics allow the present preparation to be conveniently applied topically at desired doses for therapeutic, cosmetic and nutritional purposes.

The present preparation includes the unaltered, active constituents of honey, including sugars, proteins, vitamins, enzymes, hormones, minerals and other substances. It is those active constituents that provide the preparation with its therapeutic, cosmetic and nutritional benefits. The physical characteristics of honey are modified, while keeping the active ingredients intact, to suit various applications.

The present preparation has reduced stickiness and a consistency that allows small and large doses to be applied topically without liquefaction. When applied to open wounds and sensitive tissues, irritant sensations are not experienced.

Preparations made in accordance with the present invention are based at least in part on the tissue healing capacity and the antimicrobial activity of honey. The present honey preparations are particularly effective in tissue regeneration and healing due to the presence of unaltered active constituents which are present in honey. It is those constituents that make honey effective therapeutic, cosmetic and nutritional treatments. The prominent antimicrobial activity of honey against microorganisms is due in part to the inhibine activities and related mechanisms present in honey. Due to those healing mechanisms and antimicrobial activities, the present honey preparations are superior in treatment of wounds, burns, ulcers, infections, skin, scalp and hair disorders, and other tissue conditions, including those of the eye, nose, ear and mouth.

The composition of honey is unique, as it encompasses a large profile of nutrients including sugars, amino acids, vitamins such as biotin, nicotinic acid, floic acid, pantothenic acid, pyridoxine and thiamine, enzymes such as diastase invertase, glucose oxidase and catalase, and minerals such as potassium, iron, magnesium, phosphorous, copper and calcium. Several of those components have been used individually or in combination in cosmetic or therapeutic scalp and hair preparations. In the present preparation, the complete composition of honey remains intact. When topically applied, the present preparation promotes hair growth, thickens thinning hair, prevents and reduces hair loss, treats dandruff and other scalp disorders, and softens skin. The unique honey composition provides essential nutrients to activate and regenerate hair follicles, to support strong hair growth, and to restore hair color prior to graying.

The present invention provides methods and preparations for treating skin, scalp and hair conditions using the active ingredients of honey. While it is preferred to use honey as a whole, the active ingredients may be extracted or artificially synthesized and used individually or in combinations. The present preparations are effective in treating a wide range of conditions including, but not limited to, burns, wounds, cold sores, viral infections, bacterial infections, fungal infections, acne, psoriasis, allergies, rashes, skin dryness dermatitis, poison ivy, insect bites, and similar skin conditions.

The present invention contemplates a base for other medicaments and/or cosmetic ingredients that have value to treat particular conditions.

It is a further object of the present invention to provide methods and preparations for treating skin, scalp and hair conditions wherein the treatment composition is topically applied to the skin and/or hair and hair follicles. The treatment agent includes sugar components, vitamins, minerals, proteins, enzymes and hormones existing in honey as is, extracted from bee honey, or synthesized and used individually or in mixtures.

Without the present invention, the application of honey by itself is inadequate to provide proper skin, scalp and hair dosings. The present invention contemplates methods and preparations for controlling thickness and for providing adequate dosing of the active ingredients.

Although preferred applications of the present preparation are topical for providing desired concentrations at treated areas, the treatment of the conditions may be enhanced by oral or parenteral administration of the active ingredients existing in bee honey.

While the use of whole honey is preferred, preparations including individual components, selected components, or selected components in combination with synergistically enhancing treatments are also possible.

These and further and other objects and features of the invention are apparent in the disclosure, which includes the above and ongoing written specification, with the claims.

DETAILED DESCRIPTION OF THE PREFERRED EMBODIMENTS

The disadvantages which limit the topical application of honey in cosmetics and medicine are inconveniences due to the sticky character and improper dosing of honey. Those problems are remedied in the present invention by providing compositions produced by mixing honey with oil and/or gelling agent with the aid of an emulsifier or a mixture of emulsifiers.

The present invention includes the mixing of honey or active ingredients of honey with oil, gelling agent, emulsifier and other components. Numerous mixing methods may be used including hot, warm and cold mixing methods. In preferred embodiments, cold or warm mixing is used to avoid undesirable changes due to heating the honey and to maintain the integrity of all the components including enzymes, proteins, sugars, fats, vitamins, hormones, minerals, nectar, pollen grains, and the like.

The present invention specifically contemplates methods and preparations including the active ingredients of honey in combination with optional amounts of oil, gelling or thickening agent, emulsifier, fragrance, preservative, colorant and any other component that can be used in a cosmetic or therapeutic topical application. Examples of possible natural oils include, but are not limited to, rice bran oil, corn oil, almond oil, coconut oil, castor oil, cottonseed oil, lanolin oil, and extracted or hydrogenated derivatives of those oils. Silicone oil is an example of a possible synthetic oil. Mineral oils, along with their distillates and cracked or polymerized derivatives, can partially or completely replace the oil components of the present preparations.

Gelling or thickening agent is preferably a type that can be used in pharmaceutical or cosmetic preparations to control the consistency or physical properties of the preparation. Possible thickening agents for controlling the consistency of the present preparation include, but are not limited to, natural waxes such as beeswax, carnauba wax and candela wax, paraffin waxes, hydrocarbon polymers such as polymers of ethylene and polyisobutylene, fatty acids and alcohols such as stearic acid, stearyl alcohol and lanolin alcohols, and modified waxes such as siliconyl beeswax, in addition to hydrophilic thickening and gelling agents such as carrageenan derivatives and cellulose polymers.

Of the optional components provided above, the oil is typically olive oil, although other vegetable, mineral and synthetic oils can be used individually or in combination.

When applied to the scalp and hair, the present preparation is extremely effective in promoting hair growth, preventing stopping or minimizing hair loss, thickening hair, conditioning hair and the scalp, conditioning skin, treating dandruff and alopecia, and enhancing and restoring hair to its natural color.

Methods and preparations of honey for skin, scalp, hair, lips, eyes, ears, nose and dental applications are described in detail below. Although honey is preferably used as a whole, the class of compounds existing in honey, including sugars, amino acids, vitamins such as biotin, nicotinic acid, folic acid, pantothenic acid, pyridoxine, and thiamine, enzymes such as diastase, invertase, glucose oxidase and catalase, and minerals such as potassium, iron, magnesium, phosphorous, copper and calcium, may be extracted from honey or similar natural products or synthesized chemically or modified and used individually or in combination to be formulated for topical applications or oral administration.

Honey is mixed at about 40° C. or below with an oil base selected to suit the intended application, and to control the thickness, the spreadability and the stickiness of honey. The base preferably includes one or more of the following natural, synthetic or modified natural components: oils, waxes, polymers, emulsifiers, and other optional components. Any component which is of use in therapeutic or cosmetic topical applications, and which is compatible with the desired formula, may be included and is considered under the scope of the present invention.

The following are provided as examples of the present preparation:

EXAMPLE 1

| Component | Percent by Weight | Range |
|---|---|---|
| Olive oil | 20 | 1–90 |
| Beeswax | 5 | 0.1–40 |
| Polyoxyethylene sorbitan monooleate | 3 | 0.5–20 |
| Sorbitan monooleate | 2 | 0.5–20 |
| Honey | 70 | 5–95 |
| Example 2 | | |
| Sorbitan sesquiisostearate | 4 | 0.5–20 |
| Mineral oil | 20 | 1–90 |
| Synthetic beeswax | 6 | 0–20 |
| Honey | 70 | 5–95 |

-continued

| Component | Percent by Weight | Range |
|---|---|---|
| Example 3 | | |
| Castor oil | 20 | 1–90 |
| Carnauba wax | 6 | 0.5–15 |
| Cetyl alcohol | 3 | 0.1–15 |
| Polyoxyethylene sorbitan monooleate | 6 | 1–30 |
| Honey | 65 | 5–95 |
| Example 4 | | |
| Mineral Oil | 20 | 1–90 |
| Microcrystalline wax | 2 | 0.5–15 |
| Cetyl alcohol | 3 | 0.1–20 |
| Sorbitan monoostearate | 3 | 1–20 |
| Polyoxyethylene sorbitan monoostearate | 2 | 1–20 |
| Honey | 70 | 5–95 |
| Example 5 | | |
| Yellow protopet | 16 | 1–80 |
| Beeswax | 6 | 0.5–20 |
| Sorbitan oleate | 3 | 0.5–20 |
| Honey | 75 | 5–95 |
| Example 6 | | |
| Mineral oil | 20 | 1–90 |
| Microcrystalline wax | 6 | 0.5–15 |
| Sorbitan monoostearate | 4 | 1–20 |
| Honey | 70 | 5–95 |
| Example 7 | | |
| Olive oil | 20 | 1–90 |
| Beeswax | 4 | 1–20 |
| Cetyl alcohol | 3 | 1–20 |
| TEA-dodecyl benzene sulfonate | 3 | 0.5–30 |
| Honey | 70 | 5–95 |
| Example 8 (preparation with solid emulsifying agent that act as gelling agent) | | |
| Olive oil | 25 | 1–90 |
| Sucrose stearate | 5 | 0.5–15 |
| Honey | 70 | 5–95 |
| Example 9 (preparation with reduced irritation) | | |
| Lanoline | 25 | 1–90 |
| Sucrose stearate | 5 | 0.5–20 |
| Honey | 70 | 5–95 |
| Example 10 (preparation with reduced irritation) | | |
| Mineral oil | 20 | 1–90 |
| Polyoxyethylene sorbitan monooleate | 1 | 0–20 |
| Methyl glucose dioleate | 4 | 0.5–20 |
| Honey | 75 | 5–95 |

Emulsifiers of the grillotine and grillicose group, such as sucrose stearate, methyl glucose dioleate, and glucose sesquiistearate, remove or reduce irritation when the preparation is applied to open wounds and delicate tissues such as eye tissue. Those surfactants, or similar components, are preferably used in topical applications where irritation is to be avoided.

| Component | Percent by Weight | Range |
|---|---|---|
| Olive oil | 25 | 1–90 |
| Glucose sesquiistearate | 3 | 0.5–20 |
| Methyl glucose dioleate | 2 | 0.5–20 |
| Honey | 70 | 5–95 |

The preparations disclosed in the previous examples are accomplished by mixing the oil components together with the thickening agents and emulsifying agents in mortar or glass bowls and then heated on a water bath (preferably between 60° C. and 75° C.) to melt the waxy and solid components and mix with the oil phase. Temperatures are increased or decreased as needed to suit the melting and mixing of the different components. The emulsifying agent is preferably mixed at lower temperatures after mixing the gelled oil bases, particularly when the emulsifying agent is a liquid. The emulsifying agent may also be mixed with the honey prior to mixing with the oil phase.

The entire mixture is allowed to cool to room temperature while mixing. The honey is added in portions or all at once during the mixing. Although mixing honey with oil phase is possible at temperatures above 40° C., it is preferable to perform the mixing process at 40° C. or below to avoid exposing honey to high temperatures. The oil phase can also be added to the honey and mixed in a similar fashion.

Optional components of hydrophobic nature are preferably mixed with the oil phase at proper temperature prior to adding honey. Optional components of the hydrophilic nature are preferably mixed with honey prior to mixing with the gelled oil base. It is understood that any form of mixing that is used in the cosmetic and pharmaceutical industries may be used for preparing the present formulation.

The sequence of addition of the various components, the mixing procedures, and the substitution, addition or replacement of components other than honey are not limited to those mentioned in this disclosure, but rather it is understood that the present invention is intended to include all such modifications.

In compositions where the presence of the oil phase is less important, the thickener can be a hydrophilic component including, but not limited to, natural gums such as gum arabic, gum tragacanth and guar gum, cellulose derivatives, pictins such as derivatives of alginic acid and of carragheen, bentonites and colloidal silicas, polysaccharides, synthetic macromolecules such as vinyl or acrylic groups or the like, starchy materials, phosphorylated derivatives of aliphatic hydroxylic alcohols, and natural or semi-synthetic interesterified triglycerides. The basis for overcoming the thinning and liquefication of honey is to mix honey with a gelling agent suitable for pharmaceutical, cosmetic and/or nutritional preparations. Other components for controlling the consistency, taste, color, odor and stability can also be added. The present invention further serves as a vehicle for other active ingredients which have therapeutic, nutritional or cosmetic values. The following are further examples:

Example 12

(gelled honey using carrageenan)

| Component | Percent by Volume | Range |
|---|---|---|
| Honey | 24 | 2–24 |
| Carrageenan 0.1–5% solution (gelcarin, FMC) | 1 ml | 1–23 |

Potassium chloride was added at proper concentrations to help in gel formation.

EXAMPLE 13

(gelled honey using cellulose derivatives)

| Component | Percent by Volume | Range |
| --- | --- | --- |
| Honey | 95 | 5–99 |
| Methocel 0.1–2% solution | 5 ml | 1–50 |

EXAMPLE 14

(gelled honey using polyethylene oxide polymers)

| Component | Percent by Volume | Range |
| --- | --- | --- |
| Honey | 95 | 5–99 |
| PEO1 (R.I.T.A.) 0.5–5% solution | 5 ml | 1–50 |

EXAMPLE 15

(gelled honey using polyethylene oxide polymers)

| Component | Percent by Volume | Range |
| --- | --- | --- |
| Honey | 95 | 5–99 |
| PEO27 (R.I.T.A.) 0.1–2% solution | 5 ml | 1–50 |

Water may be added at different ratios, particularly where other water soluble components are included.

EXAMPLE 16

(liquid honey preparation with reduced or no stickiness)

| Component | Percent by Weight | Range |
| --- | --- | --- |
| Lanolin oil | 5 | 0–20 |
| Vegetable oil | 15 | 0–30 |
| Sorbitan monooleate | 4 | 0–25 |
| Polyoxyethylene sorbitan monooleate | 2 | 0–25 |
| Cocamide MEA | 2 | 0–20 |
| Lauramide DEA | 2 | 0–20 |
| Sodium lauryl sulfate 40% | 5 | 0–70 |
| Honey | 70 | 5–100 |

All components except honey are warmed to melt solidified component, mixed together and cooled. The cooled mixture is then mixed with honey using a high speed mixer.

Water may be added at different ratios, especially if optional water soluble components are used.

For the purpose of topical application of honey, the preparation can take the form of a liquid, ointment, cream, lotion, shampoo, spray, soap, gel, dressing, or other acceptable form. The compositions of the present invention that are liquid or semisolid may be formed into a solution, ointment, gel ointment containing substantially no added water, or an ointment, cream or lotion containing a substantial amount of water. Compositions in the form of anhydrous ointment may be prepared as an ointment comprising freeze dried honey and beeswax and vegetable oil, freeze dried honey and a mixture of lanolin and white Vaseline, or paraffin ointment comprising freeze dried honey, beeswax, a solid paraffin and Vaseline.

EXAMPLE 17

(nonaqueous honey ointment)

| Component | Percent by Weight | Range |
| --- | --- | --- |
| dried honey | 15 | 0.1–90 |
| lanolin | 35 | 0–95 |
| white vaseline | 50 | 0–95 |

The dry honey is mixed with the lanolin. Vaseline is then added to the honey/lanolin mixture and mixed until homogenous.

The composition in the form of aerosol or spray comprises active ingredients of honey and bulking agents, natural or synthetic polymer gum to prevent dustiness, an organic solvent and a liquified hydrocarbon or hydrocarbon propellant.

EXAMPLE 18

(honey as a spray formula for local application)

| Component | Percent by Weight |
| --- | --- |
| freeze dried honey | 10 |
| volatile selicone | 13.4 |
| quaternium-18 hectorite | 0.8 |
| SD alcohol 40 anhydrous | 0.8 |
| propellant A-46 | 75 |
| fragrance | QS |

To prepare the formula, quaternium-18 hectorite is dispensed in volatile selicone in a high shear mixer for about 15 minutes. SD alcohol 40 anhydrous is then added and mixed for about 30 minutes. The mixture is then changed to low shear mixing and freeze dried honey is blended in gradually, mixing for about 15 minutes. The resulting suspension is passed through a Manton-Gaulin homogenizer at 600 p.s.i. Fragrance is added to the suspension and mixed for about 15 minutes. Cans are filled with the resulting composition and charged with propellant.

All of the examples provided in this disclosure do not serve to limit the invention in terms of ratios of honey, gelling agents, surfactants and other additives. The examples are not intended to limit the invention in terns of components, ratios or procedures. It is intended to cover all possible modifications of the invention.

Acne Treatment

Twenty-seven individuals, ages 13 and up, applied the present preparation for the treatment of acne or pimples. The preparation was applied as a thin layer in a manner similar to that of applying a regular moisturizing cream. All test subjects observed curing of the small pimples and experienced excellent skin texture when the present preparation was applied twice daily for 2–5 days. Among the test group, five males were suffering severe acne. Those 5 subjects rubbed the present preparation lightly over their entire faces once or twice a day and applied larger amounts (about 0.2 to 0.5 gram) onto large lesions at night. The large lesions were cured within one two three weeks and no new acne appeared during the course of applying the application once or twice a day. In all cases, recovery of the acne lesions occurred without leaving scars. Individuals with old dark spots, resulting after the recovery of previous acne lesions, noticed gradual change in the scar color to the normal skin color after applying the present application to the affected areas once or twice a day for one to three weeks.

Herpes and Cold Sore Treatment

Fourteen patients, ages four and up, applied the present preparation for the treatment of cold sores and herpes simplex infections on the lips. Eight subjects applied the present preparation every time they suffered from herpes or cold sores. The observations were as follows: (a) When the present preparation was applied at early stages (when subjects felt burning but before developing inflamed herpes sores) herpes was aborted in 80% of the cases and was not fully developed in the remaining 20% of the cases. (b) In cases where herpes lesions were already developed, the present preparation was lightly applied by rubbing to those lesions (about 0.05–0.2 gram). The tension and burning sensation accompanying the existing inflammation were immediately relieved. After about an hour, the crust covering the herpes lesions became soft and peeled off. The size of the lesions and the inflamed areas were significantly reduced within two hours and complete recovery was observed after three days, at most. In cases where the subjects did not use the present preparation, herpes lesions lasted for over two weeks. In a severe case of herpes simplex, one patient was suffering from severe herpes infection around his lips and surrounding face area. That patient remained home for two weeks because of the severe inflammation and swelling of his lips and face. Acyclovier, a local antiviral drug, was prescribed and used for nine days without noticeable improvement. When that patient applied the present preparation, relief from the tension and the burning was experienced within five minutes. Significant reduction of the inflammation and the swelling was observed after thirty minutes. The patient fully recovered after three days of applying the present preparation four times a day.

Wound Healing Treatment

The present preparation was used for treating 14 wounds in six individuals, three males and three females. A 42 year old male had a wound on his ram after a bike fall measuring about 2.5 cm×7 cm, with the skin layer completely peeled from the wound area. About one to three grams of the present preparation was applied to that wound two or three times a day. The wound remained clean without signs of infection. Epithelialization was promoted from the peripheries of the wound. The size of the wound decreased gradually. The wound remained fresh looking and was completely healed after two weeks. There was a complaint that the present preparation caused an irritation sensation in the open wound. When sucrose stearate or methyl glucose dioleate was employed as emulsifier, that irritation was overcome or substantially reduced. It also would have been appropriate to administer local analgesics or anesthetics. When the present preparation was applied to four small wounds, the wounds healed within 1–3 days. Two fresh sharp wounds, 1.1 cm and 1.4 cm in length, completely healed within two days when the present preparation was applied and the edges of the wound were kept adjacent using adhesive tape.

Burn Healing Treatment

The present preparation was very useful in burn treatment. The present preparation was used to treat nine burns on six individuals, three males and three females. The burns resulted from touching hot objects or from spilling hot liquids on different parts of the body. When the present preparation was quickly rubbed onto the affected skin areas after the burn incidence, the burning sensation disappeared immediately and no inflammation or complications developed. In parallel burns, where the present preparation was not applied, the burning sensation persisted, with the development of inflammation and infection in the affected areas.

The present preparation, when applied to burns of different degrees and different origins, relives pain, promotes healing and prevents and treats inflammations and infections.

Skin Allergy and Rash Treatment

Twelve individuals applied the present preparation topically to treat skin allergies, Those individuals observed relief from itching within five minutes of application. One 27 year old woman used to develop severe allergic reactions on her hands after using any dish washing soap, with the skin on her hands becoming dark, dry and itchy. When the present invention was rubbed lightly to the affected skin, the pain and itching were relieved within 15 minutes. The skin returned to its normal color after applying the present preparation twice a day for five days. That patient's allergy was prevented by applying the present preparation immediately after using the dish washing soap.

Rash resulting from different causes was also treatable and preventable when the present preparation was lightly rubbed to the rash area in children and adults of different ages.

Treatments of Other Conditions

The present preparation is highly effective in treating various other conditions, including, but not limited to, contact dermatitis, eczema, psoriasis, external viral, bacterial and fungal infections, poison ivy and insect bites. The present preparation has further applications in the treatment of any skin, scalp, hair, nose, ear, eye or dental condition. Tests have also shown the present preparation to be an extremely effective deodorant and athlete's foot treatment. When the present preparation is applied to exposed skin, insect repellant activity is evidenced.

Hair Treatment

About 216 individuals (males and females, ages 18 and older) used the present preparation to treat abnormal hair loss, to grow new hair and to relieve hair and scalp disorders. All subjects topically applied about 0.5–2.0 grams (about 0.5 to 2 cubic centimeters) of the present preparation to their scalps once or twice a day. Smaller and larger dosages are also acceptable and equally effective. All subjects were advised to use the present preparation twice daily or more by rubbing the preparation into the scalp. More frequent application is preferred but less frequent application is still effective.

Cream preparations of the present invention are preferably applied as follows. Pea-sized (1–2 grams) amounts of the preparation are rubbed into the scalp using fingertips. Rubbing should continue for about one minute. It is important that the preparation be applied to the scalp and not just the hair. Multiple doses should be applied to ensure the homogeneity of distribution. The scalp may be wetted with very little water using wet fingers prior to application. Wetting makes application easier for patients having long or dense hair. Once the preparation is applied, the hair should be combed to prevent stickiness. To stimulate hair growth, the preparation should be applied twice a day. To prevent abnormal hair loss and to maintain healthier hair and scalp, the present preparation should be applied once a day. Less frequent applications are equally effective. It is preferred that hair not be washed after application. If hair must be washed, it is recommended that the hair be washed no sooner than two hours after treatment. Shorter periods are still acceptable, but longer periods are preferred. The present invention can also be applied and left for a few minutes before showering.

Among the group of 216 subjects, 41 male subjects were at the initial stages of male type baldness and 56 male subjects were completely bald. All 97 of those subjects observed thickening and darkening of the very thin and weak hair within 1–3 days of using the present invention. After 6–8 weeks of applying the present preparation once or twice a day, new thin hairs resembling peach fuzz appeared in the thinning or bald spots, particularly at the peripheries. That new hair became thicker and darker within three to four weeks when use of the present preparation was continued. All subjects demonstrated new hair growth within two to three months of using the present preparation.

Twenty-eight subjects suffering from substantial hair loss applied the present preparation as described in the previous examples once or twice a day. Reduction of hair loss to normal or less than normal levels were reported after three applications. Only one subject still observed hair loss during the first three weeks of applying the present preparation. That subject also realized considerable increase in newly grown hair.

All seventy-three female participants reported improvements in hair thickness and general hair quality after three to five applications. Hair loss was significantly reduced after the third application when the present preparation was applied once or twice a day.

When four females suffering from hair loss with female type alopecia applied the present preparation to their scalps, new hair growth was observed within 2–3 months. New hair growth increased significantly as application of the present preparation continued. Patients (males and females) who stopped applying the present preparation also observed new hair growth subsequent to terminating application.

Fifteen males and females suffering from dandruff observed disappearance of the condition within one to two weeks when the present preparation was applied once or twice a day.

Three subjects were suffering from alopecia areata on the head, beard and mustache. When the present preparation was applied once or twice a day, considerable hair growth occurred and the affected areas were reduced in size within 2–3 months.

In all treated cases, newly grown hair and existing hair became conditioned, thicker, stronger and more attractive. Gradual original hair color restoration was observed in almost all subjects whose hair was graying including patients older than sixty within two to eight months. All individuals seeking new hair growth observed new hair growth before three months. Individuals suffering from hair loss or dandruff observed considerable improvement within a few days to two weeks.

Male and female subjects suffering from excessive hair loss observed significant reduction in hair loss after applying the present preparation two to three times. When individuals with hair apply the present preparation once or twice a week, healthier, more attractive hair results and the number of falling hair was kept below the normal level of hair loss. Other hair and scalp conditions that are treatable using the present preparation include, but are not limited to, seborrheic dermatitis, eczema and psoriasis of the scalp.

In preferred embodiments of the present invention, the preparation may be applied as a spray. A vacuum is used to dry the honey. The dried honey, along with any other components, are mixed with a propellant and expelled from a canister for easy, clean application.

The present preparation preferably includes no, or a negligible amount of, water and no artificial preservatives.

For the examples provided in the present disclosure, dosage amounts were in the range of about 0.05 and 5.00 grams.

While the invention has been described with reference to specific embodiments, modifications and variations of the invention may be constructed without departing from the scope of the invention, which is defined in the following claims.

I claim:

1. A method for preparing a honey-based topical application comprising forming a base as a carrier and mixing active ingredients of honey with the base, wherein mixing the active ingredients of honey further comprises establishing a mixing temperature of not more than forty degrees Celsius.

2. A method for preparing a honey-based topical application comprising forming a base as a carrier and mixing active ingredients of honey with the base, further comprising extracting the active ingredients from honey prior to mixing with the base.

3. A method for preparing a honey-based topical application comprising forming a base as a carrier and mixing active ingredients of honey with the base, further comprising freeze drying the active ingredients of honey and wherein the mixing comprises mixing the freeze dried active ingredients.

4. A method for preparing a honey-based topical application comprising forming a base as a carrier and mixing active ingredients of honey with the base, wherein the base comprises hydrophilic and hydrophobic substances, and wherein the base is a solid base.

5. A method for preparing a honey-based topical application comprising forming a base as a carrier and mixing active ingredients of honey with the base, wherein the base comprises hydrophilic and hydrophobic substances, and wherein the base is an aerosol base.

* * * * *